United States Patent
Wilson et al.

(10) Patent No.: US 10,806,571 B2
(45) Date of Patent: Oct. 20, 2020

(54) INFLATABLE DEVICE FOR IMPROVING PHYSIOLOGICAL CARDIAC FLOW

(71) Applicant: Harmony Development Group, Inc., Cornelius, NC (US)

(72) Inventors: John Wilson, Cornelius, NC (US); Christopher Seguin, Norton, MA (US); Nikola Cesarovic, Volketswil (CH)

(73) Assignee: Harmony Development Group, Inc., Cornelius, NC (US)

( * ) Notice: Subject to any disclaimer, the term of this patent is extended or adjusted under 35 U.S.C. 154(b) by 0 days.

(21) Appl. No.: 15/863,417

(22) Filed: Jan. 5, 2018

(65) Prior Publication Data

US 2018/0185145 A1    Jul. 5, 2018

Related U.S. Application Data

(60) Provisional application No. 62/442,856, filed on Jan. 5, 2017.

(51) Int. Cl.
*A61F 2/24* (2006.01)
*A61F 2/00* (2006.01)

(52) U.S. Cl.
CPC .......... *A61F 2/2421* (2013.01); *A61F 2/24* (2013.01); *A61F 2/2481* (2013.01); *A61F 2/2487* (2013.01); *A61F 2/0077* (2013.01); *A61F 2002/0081* (2013.01); *A61F 2220/0008* (2013.01); *A61F 2220/0025* (2013.01); *A61F 2250/0003* (2013.01); *A61F 2250/0007* (2013.01)

(58) Field of Classification Search
CPC ....................................................... A61F 2/24
See application file for complete search history.

(56) References Cited

U.S. PATENT DOCUMENTS

| 7,854,762 | B2 | 12/2010 | Speziali et al. |
| 8,092,525 | B2 | 1/2012 | Eliasen et al. |
| 8,778,017 | B2 | 7/2014 | Eliasen et al. |
| 2007/0198082 | A1 | 8/2007 | Kapadia et al. |

(Continued)

OTHER PUBLICATIONS

International Search Report and Written Opinion of the International Searching Authority from parent application PCT/US2018/12578 dated Mar. 28, 2018.

*Primary Examiner* — Matthew W Schall
(74) *Attorney, Agent, or Firm* — Stephen J. Kenny; Robert Piston; Foley Hoag LLP (57) ABSTRACT

An implant system for improving physiological cardiac flow in a human heart is provided including an inflatable implant for positioning at least partially within an atrium, a ventricle and a atrial/ventricular valve of the human heart and defining a surface for intercepting and redirecting hemodynamic flow into the ventricle, the inflatable implant defining a surface to engage the valve; a therapeutic apical base plate assembly attachable to the apex of the heart; and a tether connected between the inflatable implant and the therapeutic apical base plate assembly. The inflatable implant and the therapeutic apical base plate assembly are configured to reshape the ventricular wall by transducting cardiac force and/or energy generated by the heart during systole and diastole when the inflatable implant is engaged with the valve and of the therapeutic apical base plate assembly is attached to the apex.

19 Claims, 13 Drawing Sheets

(56) References Cited

U.S. PATENT DOCUMENTS

| | | |
|---|---|---|
| 2009/0048668 A1 | 2/2009 | Wilson et al. |
| 2009/0131849 A1 | 5/2009 | Maurer et al. |
| 2011/0022164 A1 | 1/2011 | Quinn et al. |
| 2011/0224655 A1 | 9/2011 | Asirvatham et al. |
| 2013/0325110 A1 | 12/2013 | Khalil et al. |
| 2014/0309732 A1* | 10/2014 | Solem .................... A61F 2/246 623/2.36 |
| 2014/0336751 A1 | 11/2014 | Kramer |
| 2014/0371846 A1 | 12/2014 | Wilson et al. |
| 2015/0112429 A1 | 4/2015 | Khairkhahan et al. |
| 2016/0089237 A1 | 3/2016 | Wilson et al. |

* cited by examiner

INFLATABLE DEVICE FOR IMPROVING PHYSIOLOGICAL CARDIAC FLOW

CROSS-REFERENCE TO RELATED APPLICATIONS

This application claims priority to U.S. Provisional Patent Application No. 62/442,856 filed on Jan. 5, 2017, entitled "Inflatable Device for Improving Physiological Cardiac Flow," which is hereby incorporated by reference in its entirety herein.

TECHNICAL FIELD

The present disclosure relates generally to an inflatable implant for restoring and improving physiologic intracardiac flow within the heart of a human subject.

SUMMARY

An implant system for improving physiological cardiac flow in a human heart is provided including an inflatable implant for positioning at least partially within an atrium, a ventricle and a atrial/ventricular valve of the human heart and defining a surface for intercepting and re-vectoring hemodynamic flow into the ventricle and off of the valve leaflets, the inflatable implant defining a surface to engage the valve; a therapeutic apical base plate assembly attachable to the apex of the heart; and a tether connected between the inflatable implant and the therapeutic apical base plate assembly. The inflatable implant and the therapeutic apical base plate assembly are configured to reshape the ventricular wall by transducting the atrioventricular pressure gradient, cardiac force, and/or energy generated by the heart during systole and diastole when the inflatable implant is engaged with the valve and with the therapeutic apical base plate assembly attached to the apex.

In some embodiments, the shape of the inflatable implant is adjustable to steer hemodynamic flow and transduct native atrioventriculare pressure gradient cardiac energy and/or force.

In some embodiments, the inflatable implant includes at least one chamber at least partially filled with a gas, fluid or gel, and the shape of the inflatable implant is adjustable by introduction or removal of gas, fluid or gel into a chamber of the inflatable implant.

In some embodiments, the girth of the implant is increased or decreased by introduction or removal of gas, fluid or gel into a chamber of the inflatable implant.

In some embodiments, the inflatable implant includes a wing chamber, and the position of the wing chamber is adjustable by introduction or removal of gas, fluid or gel into the wing chamber of the inflatable implant.

In some embodiments, the implant system includes a subcutaneous control unit for controlling the volume of gas, fluid or gel volume filling the inflatable implant.

In some embodiments, the surface of the inflatable implant includes one of more ridges for directing or channeling hemodynamic flow.

In some embodiments, the tether is adjustable longitudinally in order to position the inflatable implant with respect to the valve.

In some embodiments, the tether includes a plurality of longitudinally moveable shafts to adjust the longitudinal position of the inflatable implant.

In some embodiments, the tether includes an inflatable reservoir for adjusting the relative positioning of the shafts.

In some embodiments, the inflatable reservoir is sized to alter inflow blood velocity by decreasing or increasing the volume of the ventricle.

In some embodiments, the implant system includes a subcutaneous control unit for controlling the volume of gas, fluid or gel volume filling the inflatable reservoir.

In some embodiments, the therapeutic apical base plate assembly includes a securement plate and a ball joint.

In some embodiments, the therapeutic apical base plate has elongated ends or tabs that can extend over one or more chambers of the heart.

In some embodiments, the tabs deliver specific transducted force from the implant, via the tethering conduit shaft, through the therapeutic apical base plate and into the ventricular wall.

BRIEF DESCRIPTION OF THE DRAWINGS

The objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein.

DETAILED DESCRIPTION

Figure 1:
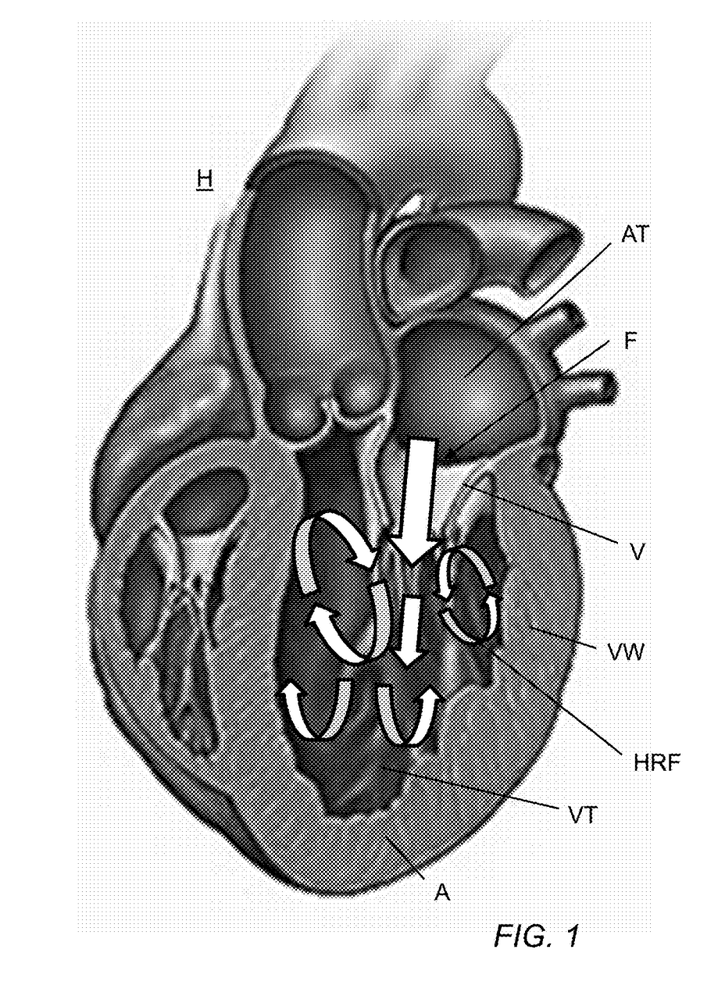
FIG. 1 is a diagram illustrating the vortex flow pattern of a healthy human heart.

One of the features of healthy heart H function is proper physiological intracardiac flow. During ventricular contraction of the ventricle VT, considerable forces are exerted on the closed atrial/ventricular valve V. These forces are transducted via the chordae tendinae and papillary muscles to the ventricular wall VW. There is a resulting valvulo-ventricular wall interaction, which provides the ventricle VT with structural support and stability by maintaining the elliptical geometry and functional support, which is pivotal for healthy intracardiac hemodynamic flow, supports the creation of healthy ventricular vortices, and delivers hemodynamic force and velocity during ventricular ejection. During ventricular diastole, the ventricular pressure rapidly decreases allowing the ventricle to fill. The pressure gradient between the atrium AT and the ventricle VT is referred to as the atrioventricular pressure gradient. As illustrated in FIG. 1, the valve V opens and blood rushes from the atrium AT into the ventricle VT through the valve orifice in the direction of flow (indicated by arrow F). The valve leaflets have a steering function, e.g., directing ventricular flow at an angle or vector to create an initial spin as illustrated in FIG. 1. Such angle may be due to the asymmetry of the valve leaflets and/or to the different shapes and sizes of the leaflets. A vortex progression results culminating in the creation of a healthy ventricular vortex. This flow of blood through the valve orifice and off the valve leaflets begins the initial spin. Further filling volume of the ventricle is partially engaged by this hemodynamic spin, such that a vortex ring is created in the ventricle VT. The resulting rotational flow or vortex, now a reservoir of kinetic energy within the ventricle, is believed significant to proper blood flow pattern, velocity and volume through and out of the heart. It is believed that the ventricular/apical countertwist initiates in diastole as the inflowing ventricular blood leaves the leaflets at vector.

Figure 2:
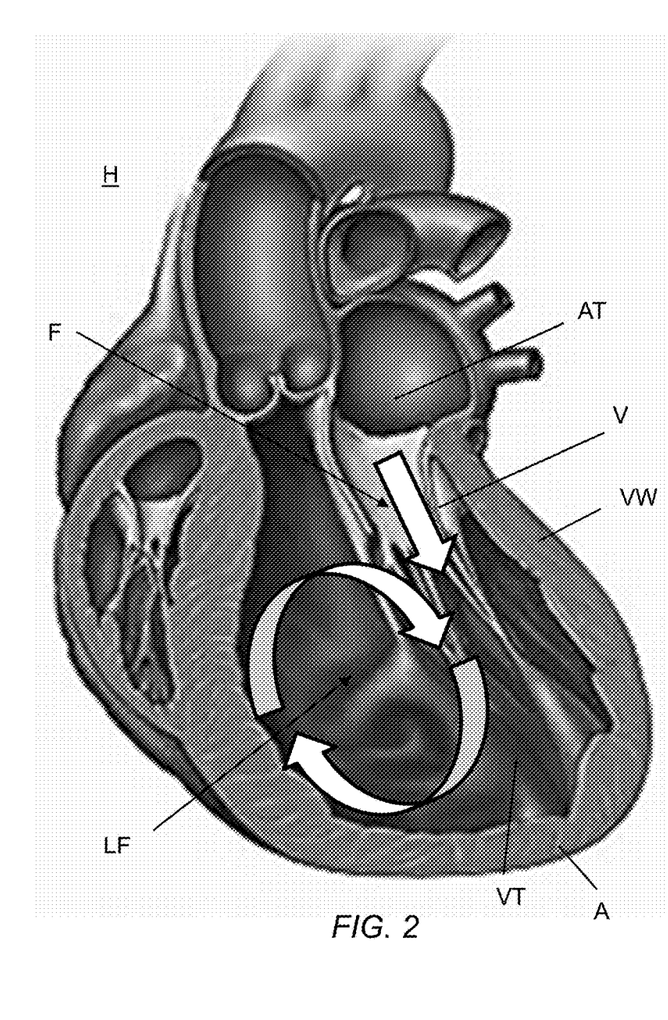
FIG. 2 is a diagram illustrating the dysfunctional vortex flow pattern of a human heart with pathology.

FIG. 2 illustrates that under certain conditions, such as dilated cardiomyopathy (DCM) in which the heart H becomes enlarged, the vortex and elliptical shape are lost, and the ventricle VT is unable to pump blood efficiently. Such conditions are marked by a low velocity outflow LF and poor cardiac output in which the vortices are abnormal or absent and geometric distortion is present.

In accordance with the disclosed subject matter, an inflatable flow/force guiding 'member' is implanted in the atrioventricular area of the heart. It is anchored at the apex of the heart and extends through the ventricle and valve orifice into the atrium. When the ventricle contracts in systole, the flow/force guiding 'member' harnesses the valvular and sub-valvular energy and force, native to the heart, via the valve's leaflets and transfers or transducts that energy and force to the apex, via the tethering conduit shaft, in the form of stretching and torsion. When the ventricle relaxes in diastole, the structure of the flow/force guiding 'member' intercepts atrial blood and re-vectors it, enabling, enhancing, or assisting the initiation of vortex (i.e., spin) as blood flows off the leaflets and drains into the ventricle. By implanting the flow/force guiding 'member', the hemodynamic vortex flow pattern that is disrupted by pathology or defect is mitigated and healthy ventricular geometry and function can be restored.

In one embodiment, the flow/force guiding 'member' is an inflatable paddle with ridges. The paddle includes one or more internal cavities for filling with inflating liquid. Such fluid is passively forced up and down in the flow/force guiding 'member' by cardiac contractions.

Figure 3:
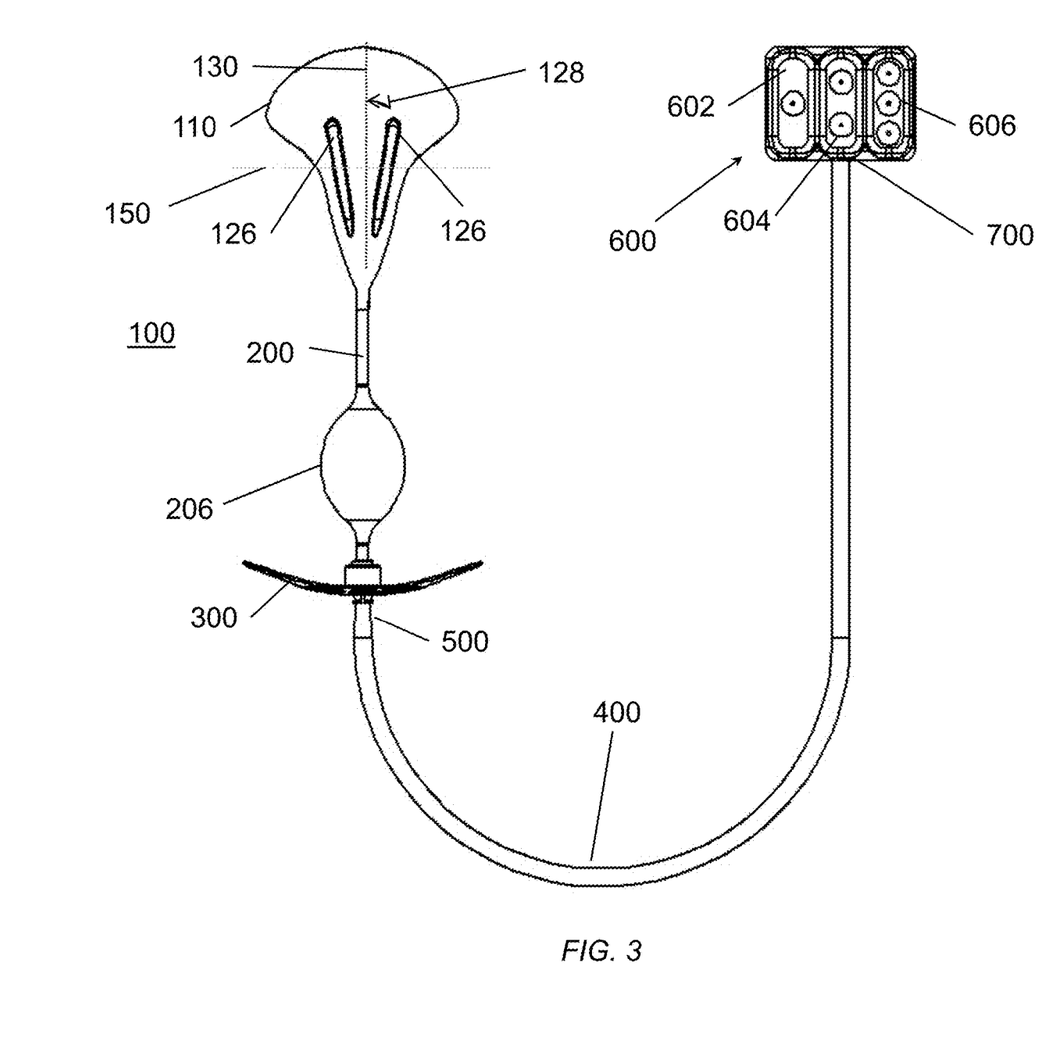
FIGS. 3-4 illustrate the system in accordance with exemplary embodiments of the disclosed subject matter.
Figure 4:
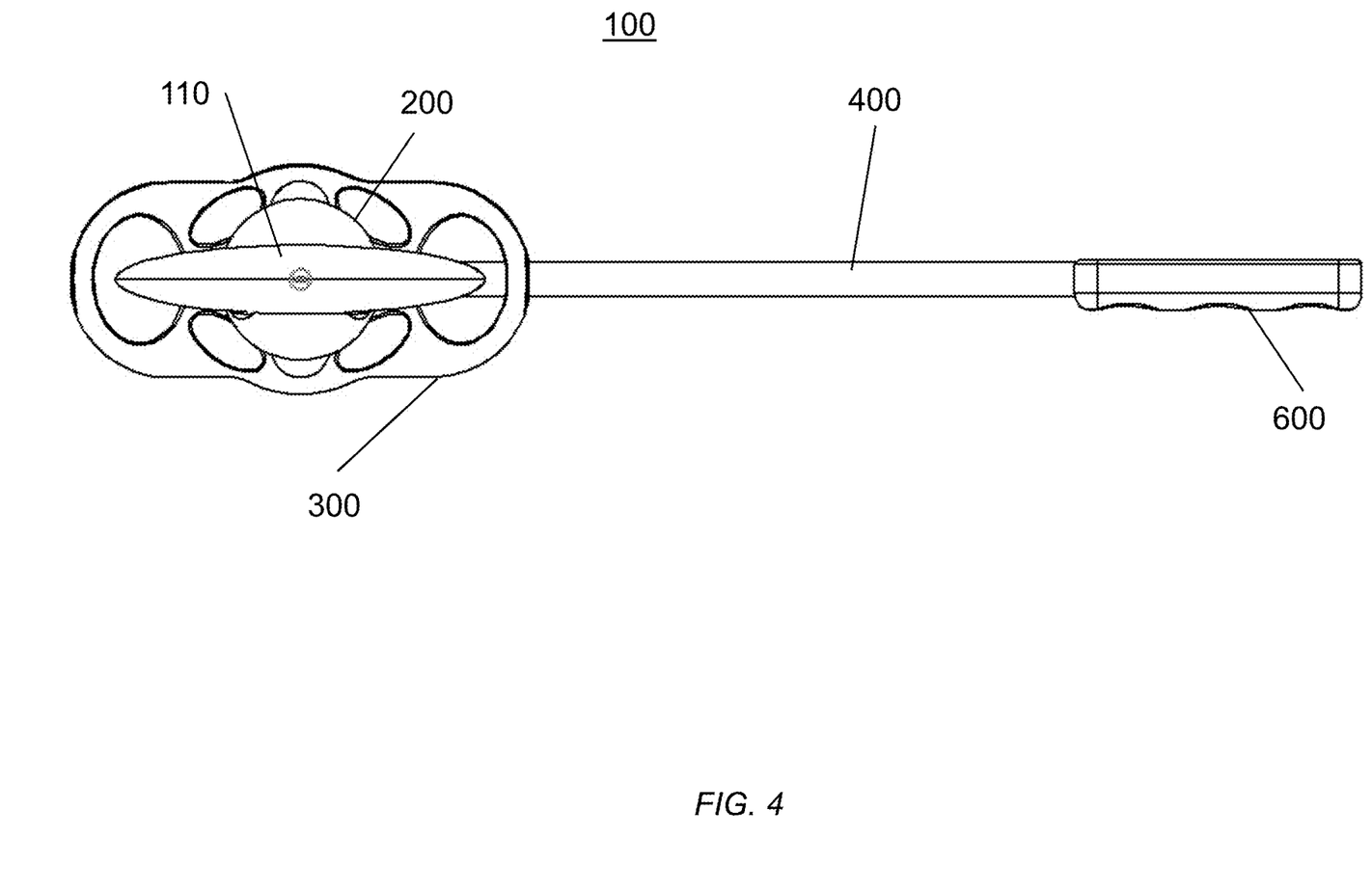

As illustrated in FIGS. 3 and 4, the implant device 100 includes a paddle, or multi chamber fluid filled flow/force guiding 'member' 110 connected to a multi-lumen transducting conduit or shaft 200 (also referred to as a force transducting tether). The member 110 is at least partially filled with a gas, fluid or gel. The transducting shaft 200 is designed to be fixed to the apex A of the heart H by a therapeutic apical base plate assembly 300. (Implantation of the device 100 in the heart H is illustrated herein below in FIGS. 17-21.) The transducting conduit or shaft 200 is connected to a multi lumen tube 400 after exiting the apex A at joint 500. In some embodiments, multi-lumen tube 400 is connected to a control unit 600 at connection 700, e.g., a joint, valve, connector or the like. Control unit 600 adjusts the device performance via a fluid communicating system when connected to the multi lumen tube 400. For example, the gas, fluid or gel provided to inflate the flow/force guiding 'member' 110 may be controlled by the control unit 600, as discussed below.

FIG. 3 illustrates that the approximate location of the line of coaptation by the valvular structure is denoted by dotted line 150.

Figure 5:
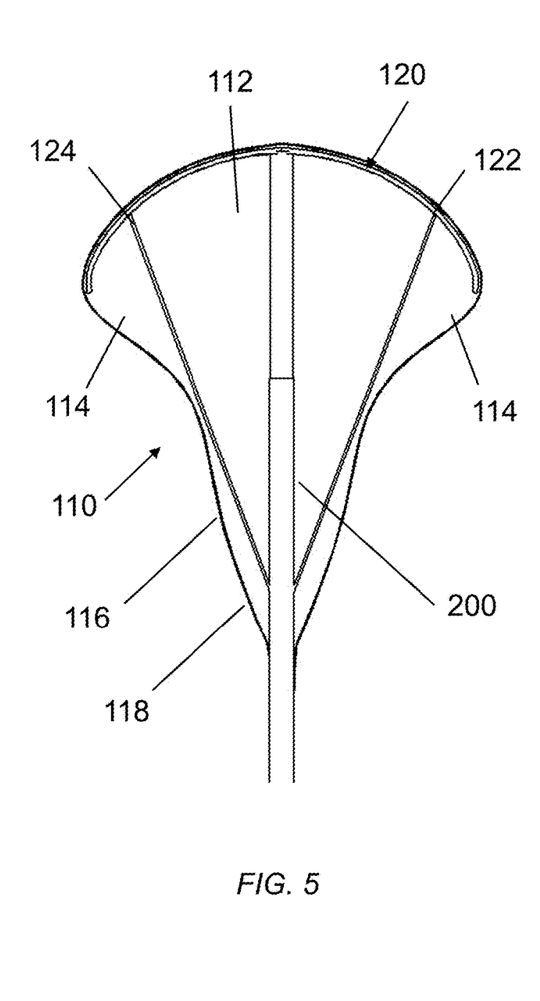
FIG. 5 is a cutaway side view of an implant flow/force guiding member in accordance with exemplary embodiments of the disclosed subject matter.

The flow/force guiding 'member' 110 is illustrated in greater detail in FIG. 5, and is designed with a portion of the exterior surfaces to intercept and redirect blood flow from the atrium AT to the ventricle VT, and a portion of the exterior surfaces to engage the valvular and subvalular structures V. The member 110 has a wider "manta"-shape portion 112 including side wings 114 at a distal end portion that tapers towards a mid-portion 116 and further towards a narrow end portion 118. The "manta"-shape portion 112 is designed to be positioned at least partially in the atrium AT, and the mid portion 114 and narrower portion 116 are designed to be positioned at least partially through the valve V and into the ventricle VT. (See also, FIGS. 17-21 below.) In some embodiments, member 110 includes a lateral ('wing to wing') shape support structure, e.g., a skeletal crescent beam 120, fixed to the distal end of the shaft 200 and having two force-transducting trusses 122, 124 connecting to the proximal end of the shaft 200 inside of the flow/force guiding 'member' 110 to aid in the transduction of captured atrioventricular pressure gradient force. The surface of the "manta"-shape portion 112 of the flow/force guiding 'member' 110 intercepts atrial blood and re-vectors it to enhance or restore natural physiologic blood flow vector passing blood over the valve leaflets and into the ventricle VT.

Figure 6:
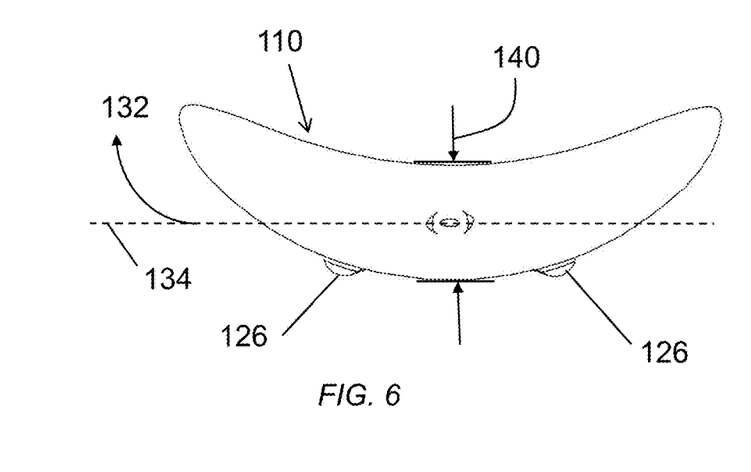
FIGS. 6 and 7 are distal end views of the implant flow/force guiding member of FIG. 5 disposed in anterior and posterior articulation in accordance with exemplary embodiments of the disclosed subject matter.
Figure 7:
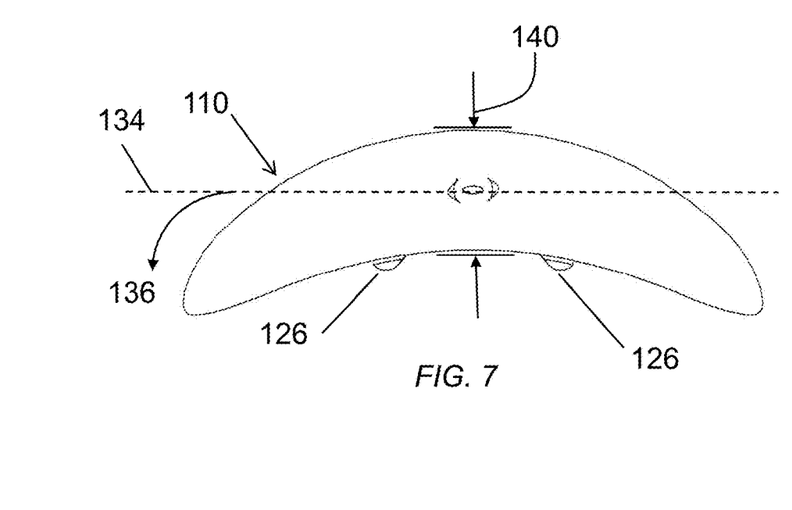
Figures 8, 9:
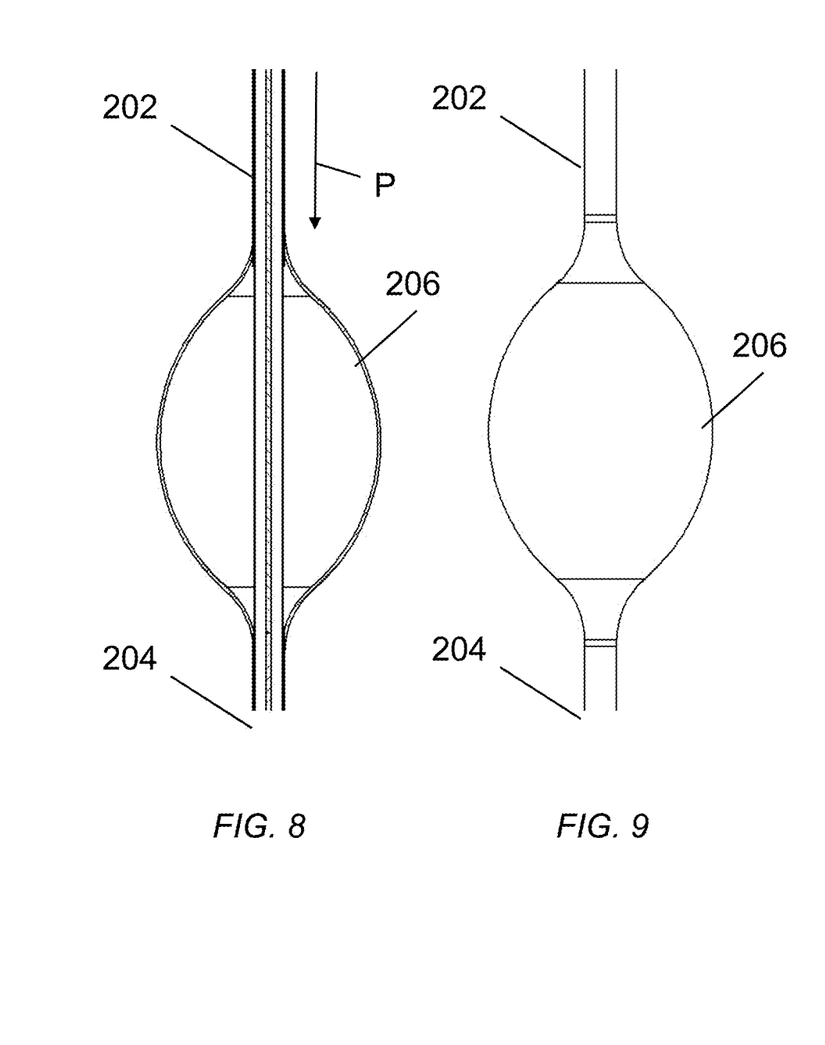
FIG. 8 is a cutaway view of the transducting conduit or shaft with the reservoir or balloon inflated in accordance with exemplary embodiments of the disclosed subject matter.
FIG. 9 is an axial view of the transducting conduit or shaft with the reservoir or balloon inflated in accordance with exemplary embodiments of the disclosed subject matter.

With reference to FIGS. 3, 6 and 7, the surface of the flow/force 'member' 110 further includes flow channel creating ribs or ridges 126 disposed thereon. As illustrated in FIG. 3, ribs 126 run at angle 128 with respect to the longitudinal axis 130 of the flow/force guiding 'member' 110, and redirect the intercepted flow of blood onto the valve leaflets, and helps facilitate proper vector upon entry into the ventricle VT. This hemodynamic re-vector may restore or assist the natural physiologic vector thereby facilitating the restoration of ventricular vortex, critical to physiologic healthy flow. As will be described in greater detail below, the shape of flow/force guiding 'member' 110 is adjustable to direct hemodynamic flow and transduct cardiac energy (atrioventriculare pressure gradient) and/or force. For example, flow/force guiding 'member' 110 can include a fluid chamber, in which fluid is added or removed to create crescent-shaped articulation in the wings 114 of member 110, either anterior deflection (arrow 132) from lateral axis 134 (See FIG. 6) or posterior deflection (arrow 136) from lateral axis 134 (See FIG. 7), to better vector the intercept of atrial blood by introducing fluid into the 'wing' chambers.

The flow/force guiding 'member' 110 is designed to be positioned at least partially in the atrium AT, to extend through the valvular and subvalular structures V and at least partially in the ventricle VT. The girth of the member is selected such that a portion of the exterior surface of the flow/force guiding 'member' 100 engages the valvular and subvalular structures V, e.g., at the line of coaptation 150. (For exemplary purposes, the girth dimension of the flow/force guiding 'member' 110 generally extends perpendicular to the lateral axis 134. See, e.g., exemplary girth dimension 140 FIGS. 6-7.) The flow/force guiding 'member' 110, when positioned, captures the native cardiac force and/or energy of the atrioventricular pressure gradient as the valvular and subvalular structures V coapt or 'grab and pull' on the flow/force guiding 'member' 110 in systole. The 'grab and pull' is a result of the pressure gradient between the ventricle and atrium. When the leaflets are applying force to the member 110 the ventricle is at a higher pressure then the atrium. Increasing the girth of the member increases the cross-sectional area of the member generally in the lateral axis 134. The increased girth in turn increases the area the member has available to capture the atrial-ventricular pressure gradient. This increases the force transducted to the apical base plate 302. Introduction or removal of gas, fluid or gel into the flow/force guiding 'member' 110 provides a secure engagement of the flow/force guiding 'member' 110 with the valvular and subvalular structures V and increases or decreases the amount of energy and force that is transducted.

Figures 10, 11:
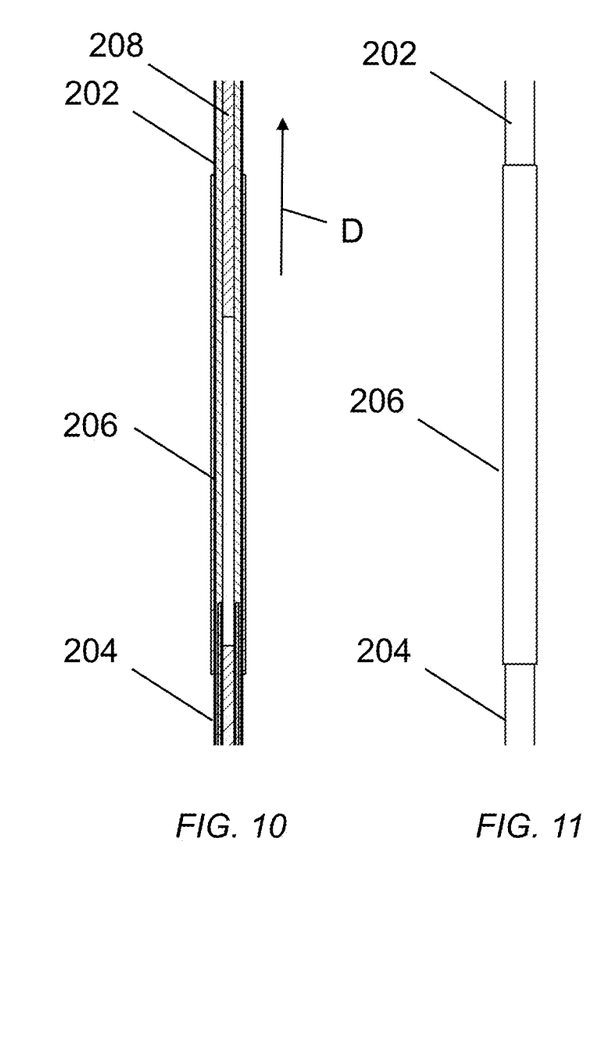
FIG. 10 is a cutaway view of the transducting conduit or shaft with the reservoir or balloon deflated in accordance with exemplary embodiments of the disclosed subject matter.
FIG. 11 is an axial view of the transducting conduit or shaft with the reservoir or balloon deflated in accordance with exemplary embodiments of the disclosed subject matter.
Figure 12:
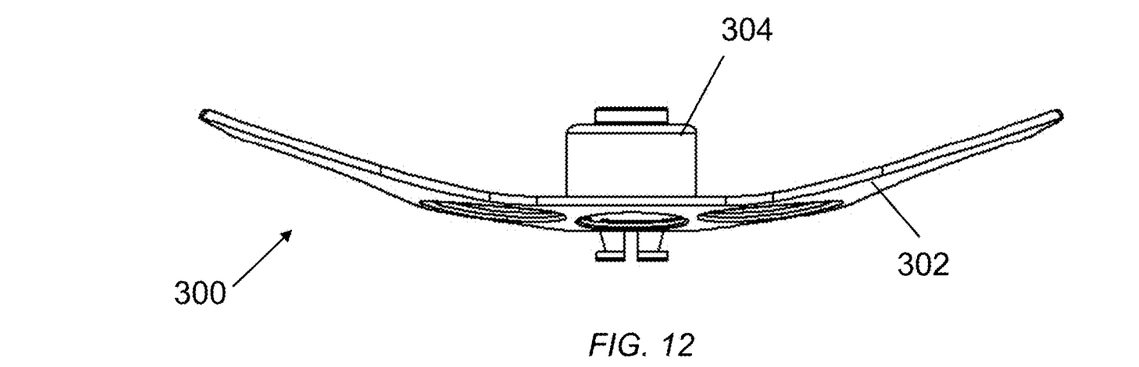
FIG. 12 is a side view of the therapeutic apical base plate assembly in accordance with exemplary embodiments of the disclosed subject matter.
Figure 13:
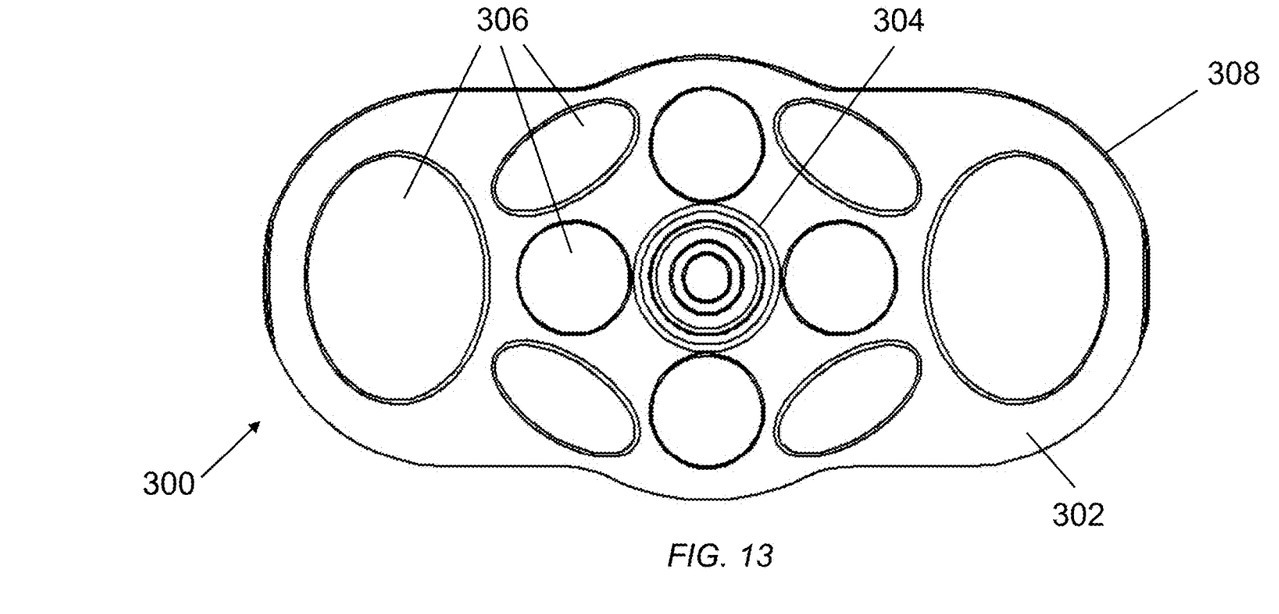
FIG. 13 is top view of the therapeutic apical base plate assembly in accordance with exemplary embodiments of the disclosed subject matter.
Figure 14:
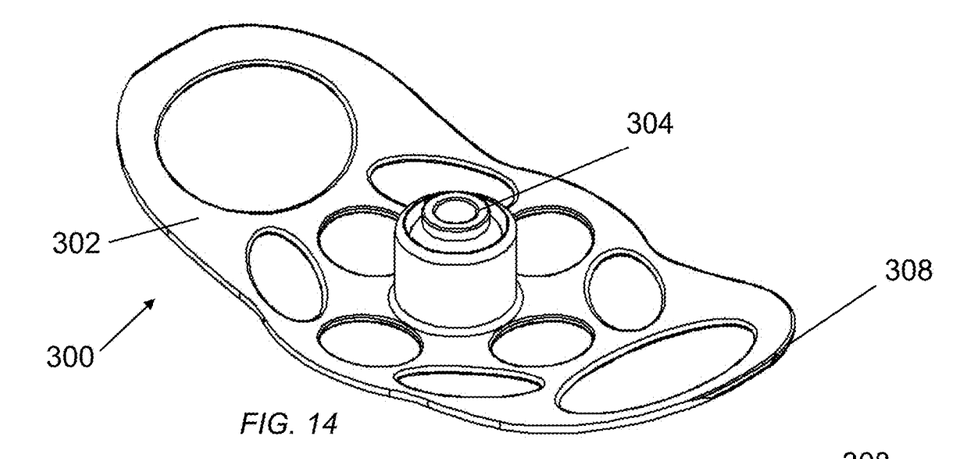
FIG. 14 is perspective view of the therapeutic apical base plate assembly in accordance with exemplary embodiments of the disclosed subject matter.
Figure 15:
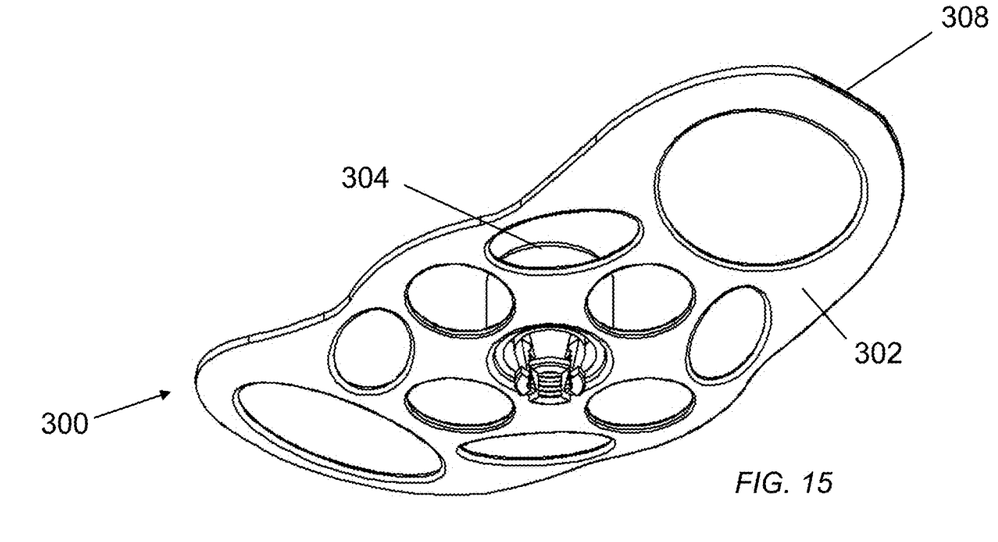
FIG. 15 is perspective view of the therapeutic apical base plate assembly in accordance with exemplary embodiments of the disclosed subject matter.

Tethering conduit shaft 200 can be used to longitudinally adjust flow/force guiding 'member' 110 for more precise positioning within the heart. As illustrated in FIGS. 8-11, shaft 200 includes a plurality of concentric shafts, e.g., a movable shaft 202 and a fixed shaft 204. Shafts 202 and 204 are axially moveable with respect one another (as illustrated in FIG. 10 in cross-section). An integrated inflatable reservoir or balloon 206 is supported at one end by shaft 204 and at the other end by shaft 202. Inflation of reservoir or balloon 206 by fluid introduced into the reservoir or balloon 206 provides longitudinal movement of shaft 202 with respect to shaft 204, thereby facilitating longitudinal placement of the flow/force guiding 'member' 110 with the ventricle and valve of the heart. With reference to FIG. 3, the introduction and/or removal of fluid from reservoir or balloon 206 allows adjustment of the location of flow/force guiding 'member' 110 with respect to coaptation denoted by line 150. For example, when the balloon 206 is inflated, e.g., fluid added (FIGS. 8-9), the shaft 202 is displaced proximally (arrow P) moving the flow/force guiding 'member' 110 (connected to shaft 202) in a proximal direction. Conversely, when the balloon 206 is deflated, e.g. fluid removed (FIGS. 10-11), the shaft 202 is displaced distally (arrow D) moving the flow/force guiding member 110 in a distal direction. Shaft 208 is a multi-lumen shaft that maintains fluidic communication with flow/force guiding 'member' 110. In some embodiments, the inflatable reservoir or balloon 206 is sized to decelerate inflow blood velocity by reducing ventricular volume, e.g., removing excess ventricular volume, creating a 'neo-apex,' facilitating the restoration or formation of healthy ventricular vortex which can lead to the restoration of proper intracardiac hemodynamic flow.

FIGS. 12-15 illustrates therapeutic apical base plate assembly 300 including the base plate 302 and a ball-jointed portion 304. In some embodiments, round oval cutouts 306 are defined in the base plate 302 to allow fibrous tissue in-growth for long-term security.

Figure 16:
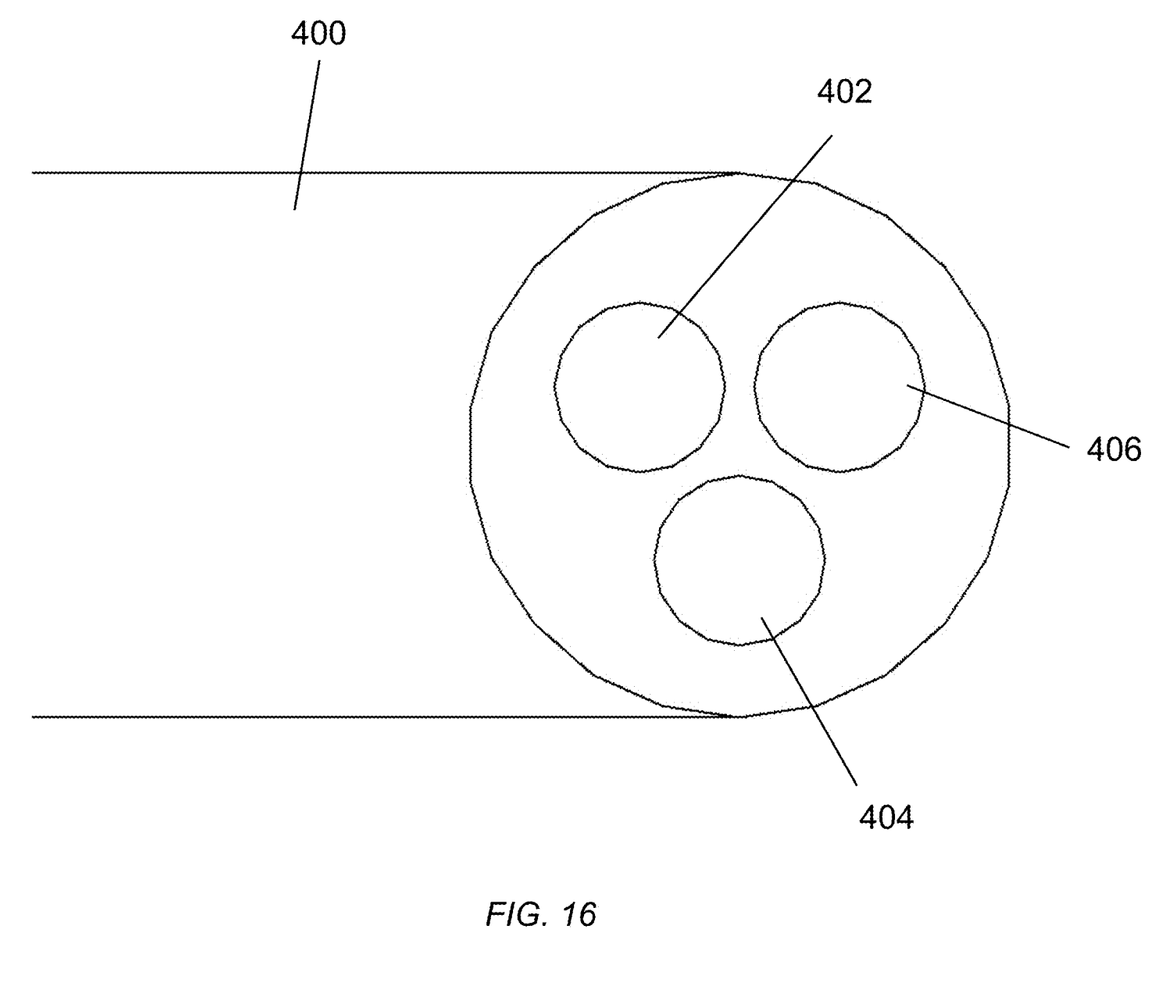
FIG. 16 is a view in partial section of the multi-lumen tube in accordance with exemplary embodiments of the disclosed subject matter.
Figure 17:
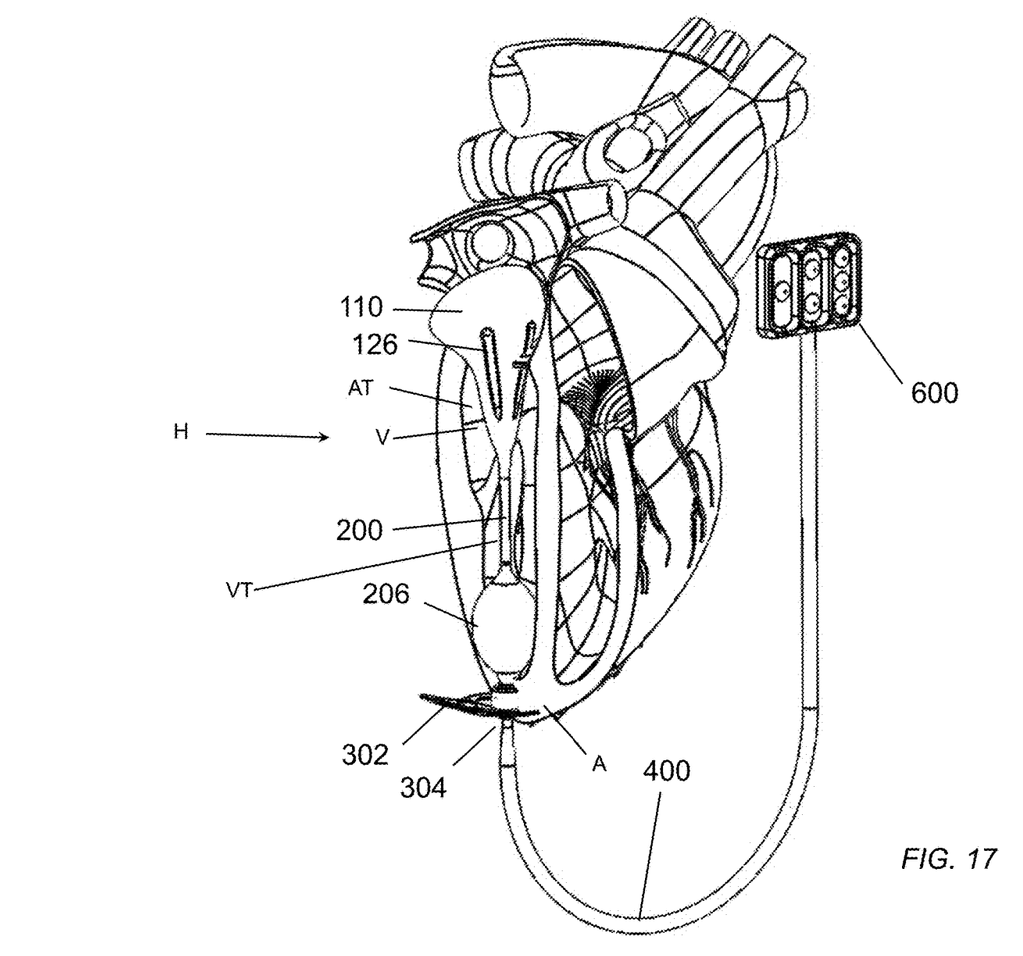
FIGS. 17-21 are views in partial section of the system of FIGS. 3-4 installed in the human heart in accordance with exemplary embodiments of the disclosed subject matter.
Figure 18:
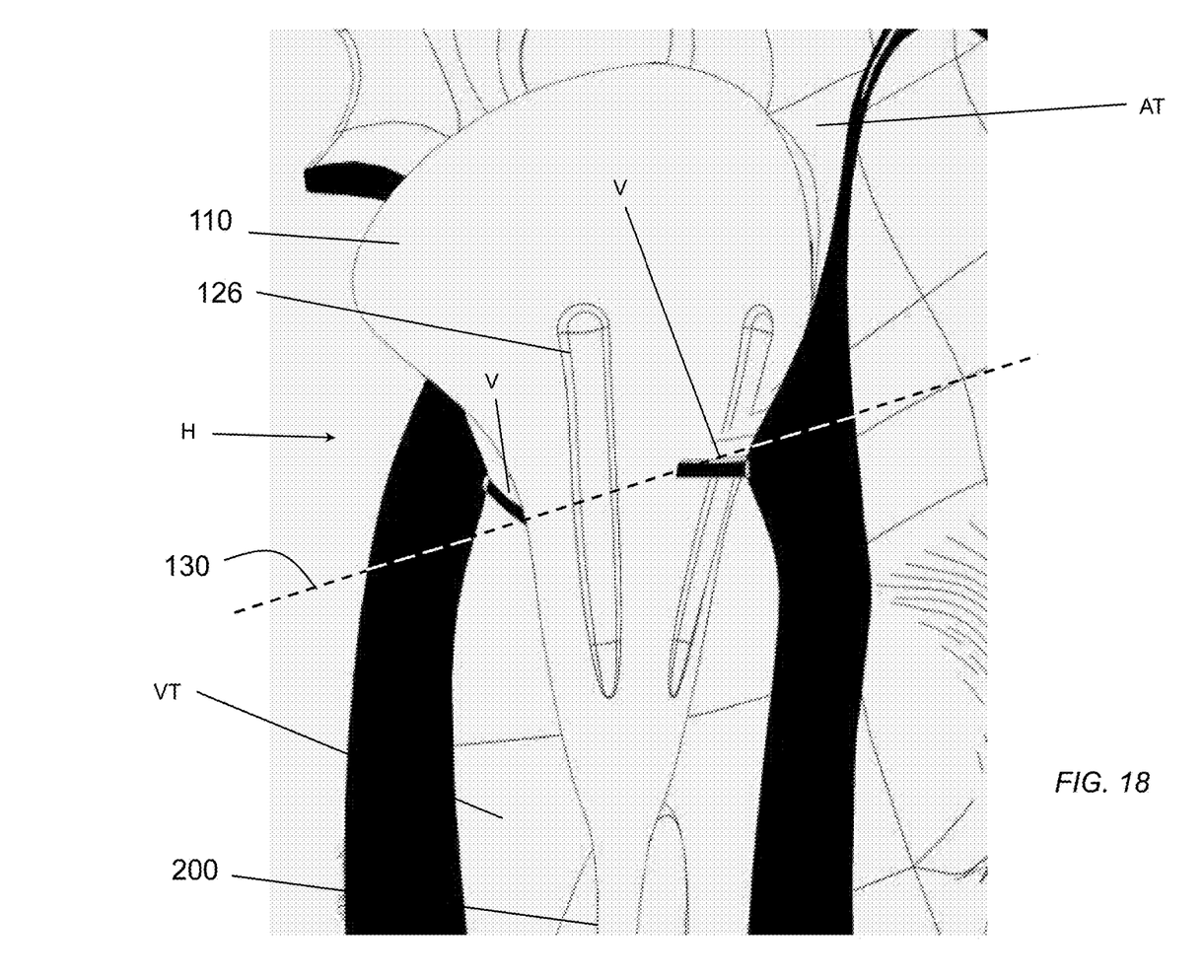
Figure 19:
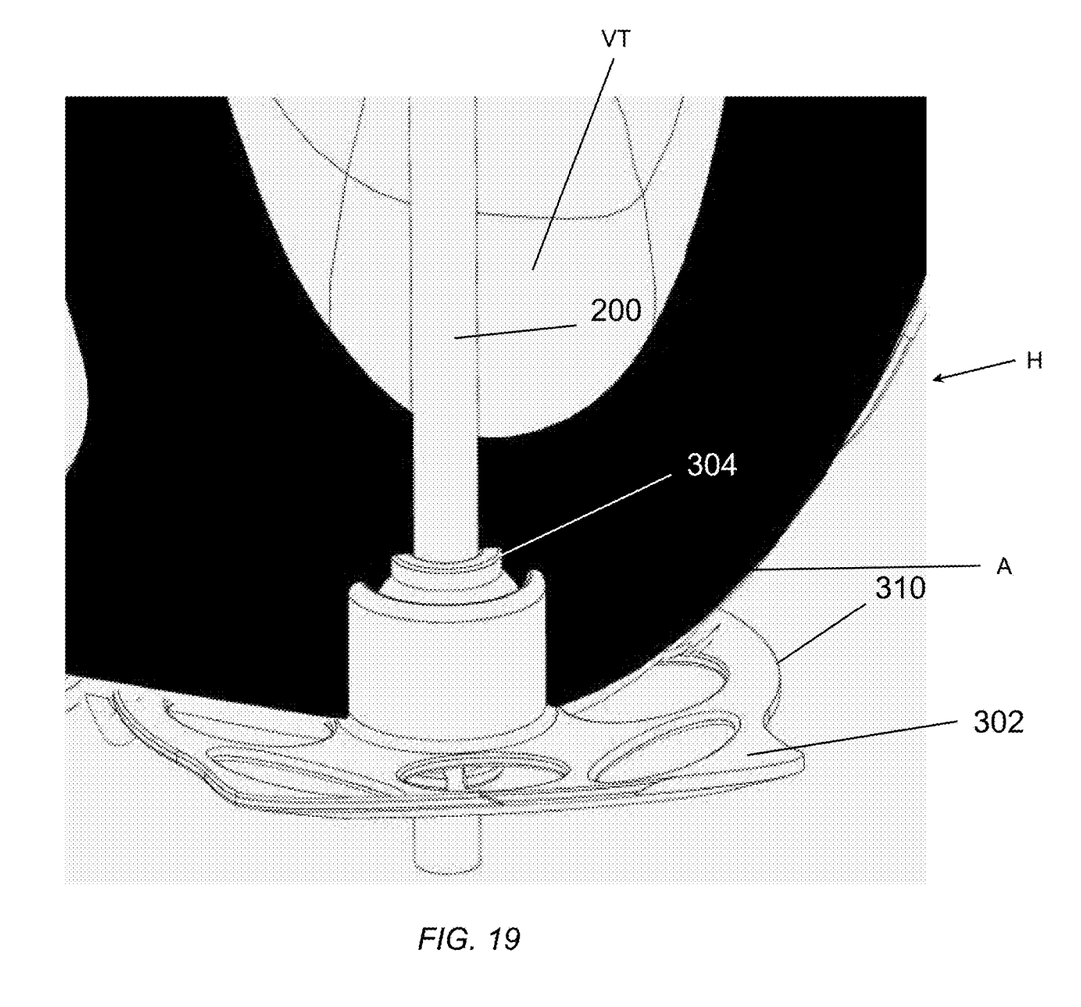
Figure 20:
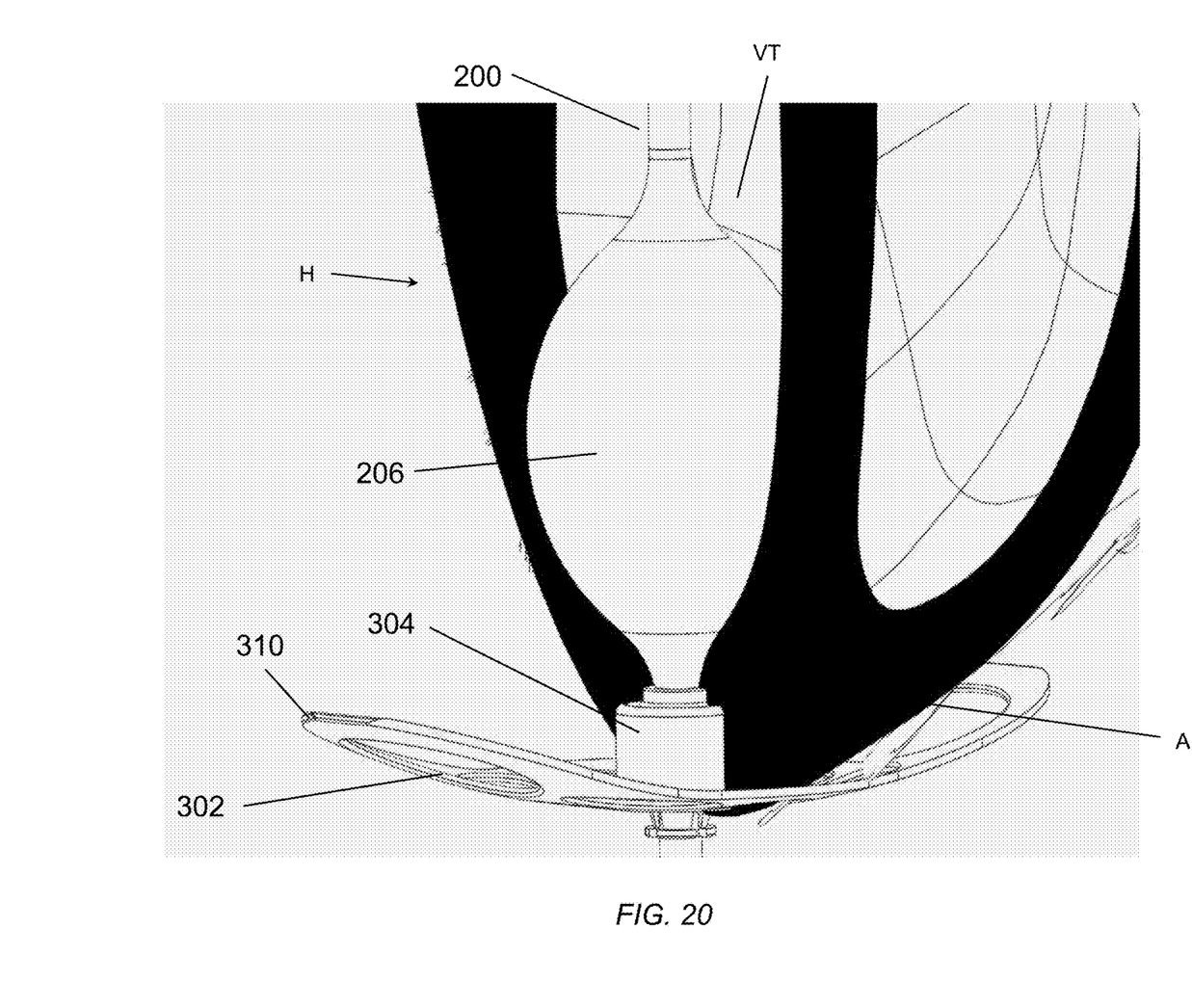

With reference to FIGS. 3 and 17, the control unit 600, which is implanted in the patient beneath the skin and accessible for palpation by the surgeon, is provided to adjust the shape of flow/force guiding member 110. In some embodiments, control unit 600 is provided with three independent contained chambers 602, 604 and 606, each identifiable below the skin in some embodiments by palpable protrusions, one palpable protrusion for chamber one 602, two palpable protrusions for chamber two 604, and three palpable protrusions for chamber three 606. A connection point 700 places the control unit 600 in fluid communication, via the tube 400 and shaft 200, with the flow/force guiding 'member' 110. As illustrated in FIG. 16, tube 300 includes a plurality of lumens 402, 404, and 406 in respective fluid communication with chambers 602, 604 and 606. Control unit 600 has a needle access pad to allow introduction or removal of fluid by the surgeon to control inflation and deflation of the flow/force guiding 'member' 110 and/or balloon 206. The control unit 600 may be fabricated of ePTFE, non-porous, or any semi-porous material, to allow fibrous tissue ingrowth (the body's method of preventing infection and facilitating hemostasis).

In some embodiments, fluid is introduced to or removed from chambers 602, 604 and 606 as discussed below to adjust the shape of flow/force guiding 'member' 110. In chamber 602, fluid is introduced or removed to increase or decrease the girth or width of flow/force guiding 'member' 110. Increasing or decreasing the girth of flow/force guiding 'member' 110 alters the vector and adjusts the amount of force transducted to the ventricle VT by flow/force guiding 'member' 110. In chamber 604, fluid is introduced or removed from the integrated inflatable axial adjusting balloon 206 to axially position shafts 202 and 204 as reverse re-modeling occurs.

In some embodiments, flow/force guiding 'member' 110 includes wing chambers. The wing chambers are internal compartments along the lateral axis that can be inflated or deflated to adjust the curvature of the inflatable implant In chamber 606, fluid is added to or removed from the wing chambers of flow/force guiding 'member' 110 to create crescent-shaped articulation in the wings 114 of member 110, anterior (see FIG. 6) or posterior (see FIG. 7), to better vector the intercept of atrial blood. Changing the shape of flow/force guiding 'member' 110 affects or alters the vector at which blood flows and passes off a leaflet of the valvular structure V.

Figure 21:
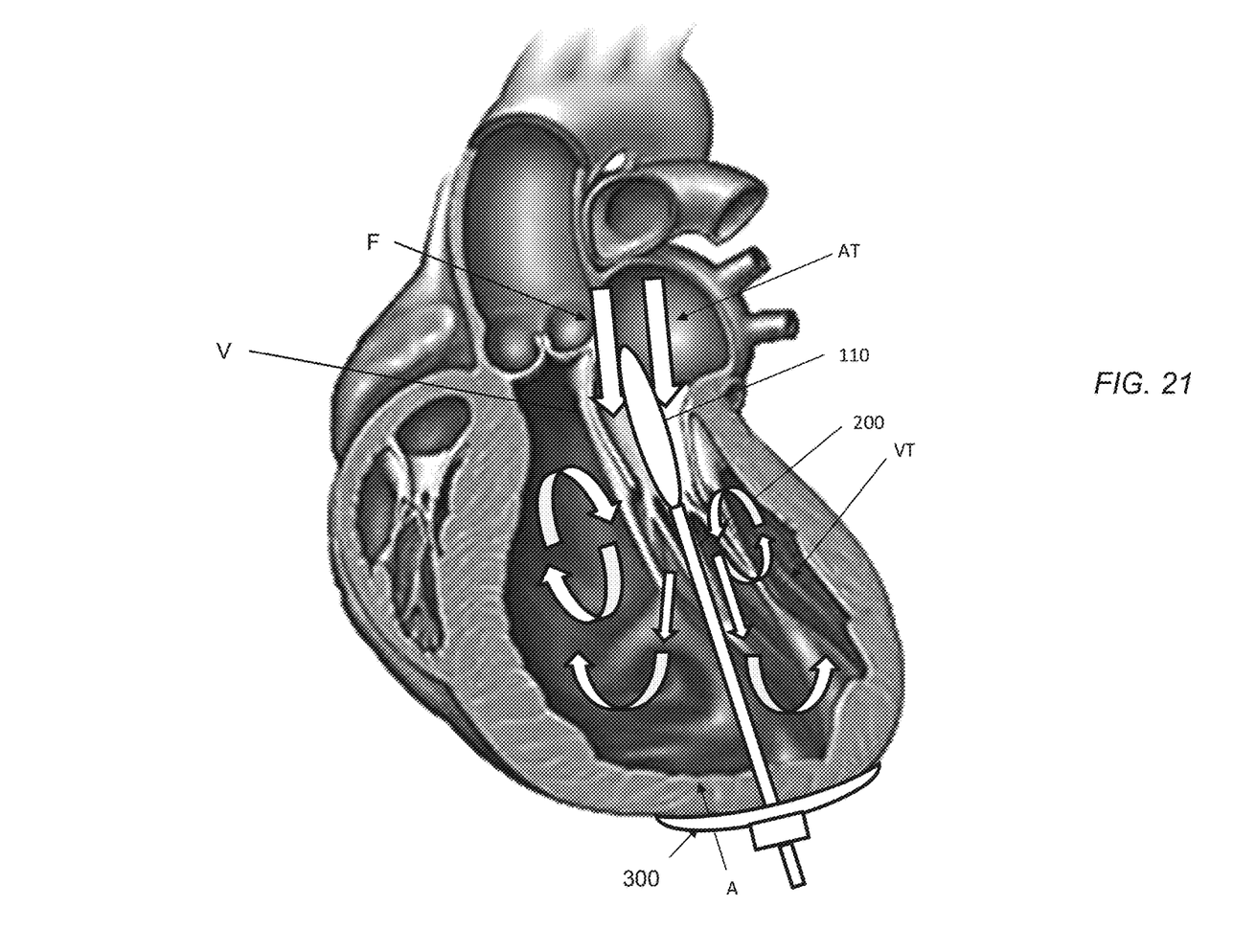

FIGS. 17-20 illustrate placement of the implant 100 in the heart H of a subject. The engagement of the flow/force guiding 'member' 110 with the valvular structures V and the therapeutic apical base plate assembly 300 with the apex A transducts atrioventricular pressure gradient or cardiac force and/or energy generated by the heart during systole to reshape the ventricular wall. For example, the 'grabbing and pulling' of the member 110 by the valvular structures V replaces lost valvulo-ventricular interaction by transducting this native force via the apical base plate 302, connected via a ball-jointed portion 304 which then, by tether to and contact with the apex A and ventricle VT, delivers physiologic natural energy and force into the ventricular structures thereby inducing reverse remodeling (positive geometric reshaping) of that ventricular structure VT. The base plate 302 utilizes specific edge shapes 308 to tailor the transducting of force to the apex A. For example, the edge shape 308 can include elongated ends or tabs that can extend over one or more chambers of the heart. When implanted, the tabs deliver specific transducted force from the implant, via the tethering conduit shaft, through the therapeutic apical base plate and into the ventricular wall. By virtue of the positioning of the flow/force guiding 'member' 110 in the valvular and subvalular structures V, the base plate 302 pulls the apex A upward in systole and releases the apex A in diastole and, in conjunction with the elongated therapeutic extensions 310 of the apical base plate 302 extending up the sides of the ventricle VT, impart by contact specific shape and fixation this transducted energy into said ventricle VT, inducing a physiologic response by replacing abnormal or lost valvulo-ventricular interaction required to maintain healthy geometric ventricular shape. As illustrated in FIG. 21, healthy high velocity rotational flow and/or vortical flow is restored in the subject's heart H. Compare with FIG. 2, above.

It will be appreciated that the methods and systems described above are set forth by way of example and not of limitation. Numerous variations, additions, omissions, and other modifications will be apparent to one of ordinary skill in the art. Thus, while particular embodiments have been shown and described, it will be apparent to those skilled in the art that various changes and modifications in form and details may be made therein without departing from the spirit and scope of this disclosure and are intended to form a part of the disclosure as defined by the following claims, which are to be interpreted in the broadest sense allowable by law.

What is claimed is:

1. A flow-vectoring implant for altering physiological intracardiac flow in a human heart, the flow-vectoring implant comprising:
    a structural member comprising a central member extending from a proximal end to a distal end, a beam disposed perpendicularly at the distal end of the central member, the beam extending from a first end to a second end, the first and second ends each curving towards the proximal end;
    an inflatable paddle operably coupled to the structural member and comprising one or more chambers for receiving an inflating fluid, the inflatable paddle extending from the proximal end of the central member to the distal end of the central member, the inflatable paddle having an anterior side and a posterior side, the inflatable paddle including a proximal portion, an intermediate portion, and a distal portion,
    a tether having a proximal end, a distal end, and a conduit therethrough, the distal end of the tether operably coupled to the proximal end of the inflatable paddle; and
    an apical base plate assembly operably coupled to the proximal end of the tether;
        wherein the proximal portion tapers distally from a first diameter at the proximal end to a second diameter at a first intermediate position of the inflatable paddle, wherein the second diameter is greater than the first diameter,
        wherein the intermediate portion tapers distally from the second diameter at the first intermediate position of the inflatable paddle to a third diameter at a second intermediate position of the inflatable paddle, the second taper rate greater than the first taper rate, the third diameter greater than the second diameter;
        wherein the distal portion tapers distally from the third diameter at the second intermediate position of the inflatable paddle to the first diameter at the distal end,
        wherein the inflatable paddle and the apical base plate assembly are configured to reshape the ventricular wall by transducting cardiac forces of the heart when the inflatable paddle is engaged with a valve and the apical base plate assembly is attached to an apex of the heart.

2. The flow-vectoring implant of claim 1, wherein the proximal portion tapers at a first taper rate and the intermediate portion tapers at a second rate that is greater than the first taper rate.

3. The flow-vectoring implant of claim 2, wherein the distal portion tapers at a third taper rate and in the opposite direction from the taper of the proximal portion and the intermediate portion.

4. The flow-vectoring implant of claim 1, wherein the structural member further comprising a first force transducting truss and a second force transducting truss each extending from the central member to the beam.

5. The flow-vectoring implant of claim 1, wherein the intermediate portion and the distal portion of the inflatable paddle together define a manta-shape.

6. The flow-vectoring implant of claim 1, wherein a shape of the inflatable paddle is adjustable by introduction or removal of the inflatable fluid in the one or more chambers.

7. The flow-vectoring implant of claim 6, wherein the one or more chambers defines a first wing chamber and a second wing chamber, and inflation of the first wing chamber causes the inflatable paddle to adopt a crescent-shaped deflection towards the anterior side of the inflatable paddle.

8. The flow-vectoring implant of claim 7, wherein inflation of the second wing chamber causes the inflatable paddle to adopt a crescent-shaped deflection towards the posterior side of the inflatable paddle.

9. The flow-vectoring implant of claim 1, wherein the inflating fluid comprises a gas, fluid, or gel.

10. The flow-vectoring implant of claim 1, further comprising one or more ridges along the posterior side of the inflatable paddle.

11. The flow-vectoring implant of claim 1, further comprising one or more ridges along the anterior side of the inflatable paddle.

12. The flow-vectoring implant of claim 1, wherein the apical base plate assembly comprises a curved shape.

13. The flow-vectoring implant of claim 12, wherein the apical base plate assembly is oriented perpendicularly to the tether.

14. The flow-vectoring implant of claim 12, wherein the apical base plate assembly comprises a plurality of cutouts configured to allow ingrowth of tissue.

15. The flow-vectoring implant of claim 12, further comprising a balloon disposed along the tether.

16. The flow-vectoring implant of claim 12, wherein the tether comprises a plurality of longitudinally moveable shafts configured to adjust a longitudinal position of the flow-vectoring implant.

17. The flow-vectoring implant of claim 12, wherein the apical base plate assembly comprises a securement plate and a ball joint.

18. The flow-vectoring implant of claim 12, wherein the apical base plate assembly comprises one or more elongated extensions configured to extend over one or more chambers of a heart.

19. The flow-vectoring implant of claim 12, further comprising:
- a tube comprising a plurality of lumens, a proximal end, and a distal end, the distal end of the tube coupled to the apical base plate assembly; and
- a control unit coupled to the proximal end of the tube and in fluid communication with the flow-vectoring implant.

* * * * *